United States Patent
Ejlersen

(10) Patent No.: US 6,994,691 B2
(45) Date of Patent: Feb. 7, 2006

(54) INJECTION APPARATUS

(75) Inventor: Henning Munk Ejlersen, Vedbaek (DK)

(73) Assignee: PreciSense A/S, (DK)

( * ) Notice: Subject to any disclaimer, the term of this patent is extended or adjusted under 35 U.S.C. 154(b) by 390 days.

(21) Appl. No.: 10/370,104

(22) Filed: Feb. 21, 2003

(65) Prior Publication Data

US 2003/0171716 A1    Sep. 11, 2003

(30) Foreign Application Priority Data

Feb. 27, 2002    (GB) .................................. 0204640

(51) Int. Cl.
*A61M 5/00*    (2006.01)

(52) U.S. Cl. .................................................. 604/117

(58) Field of Classification Search ........ 604/115–117, 604/179, 180, 171, 174, 175, 178
See application file for complete search history.

(56) References Cited

U.S. PATENT DOCUMENTS

| | | | | |
|---|---|---|---|---|
| 2,660,169 A | * | 11/1953 | Malm | 604/157 |
| 2,743,723 A | * | 5/1956 | Hein | 604/115 |
| 3,324,854 A | * | 6/1967 | Weese | 604/115 |
| 4,299,219 A | * | 11/1981 | Norris, Jr. | 604/115 |
| 4,573,970 A | * | 3/1986 | Wagner | 604/115 |
| 4,600,403 A | * | 7/1986 | Wagner | 604/115 |
| 5,364,362 A | * | 11/1994 | Schulz | 604/115 |
| 5,415,647 A | * | 5/1995 | Pisarik | 604/115 |
| 6,309,374 B1 | | 10/2001 | Hecker et al. | |
| 6,652,487 B1 | * | 11/2003 | Cook | 604/115 |

FOREIGN PATENT DOCUMENTS

| | | |
|---|---|---|
| WO | WO 00/02048 | 1/2000 |
| WO | WO 01/76665 | 10/2001 |
| WO | WO 02/30275 | 4/2002 |

* cited by examiner

*Primary Examiner*—Sharon Kennedy
(74) *Attorney, Agent, or Firm*—Nixon & Vanderhye PC

(57) ABSTRACT

An injection apparatus is described for making an injection at a predetermined depth in skin, including: a skin positioning member for positioning on a patch of skin within an area of skin such that at least a part of the patch of skin may be held elevated above or depressed below the area of skin, an injection needle, and a guidance mechanism for guiding the injection needle to slide beneath the skin positioning member to an injection position in which the distal end of the needle lies at a predetermined distance below the skin positioning member. An injection apparatus is also described including a detachable marker unit and a securing element for securing the marker unit at an injection site prior to the making of an injection to mark the position of the injection site.

23 Claims, 7 Drawing Sheets

INJECTION APPARATUS

The present invention relates to injection apparatus and to a method of injection.

Cutaneous injection is used in a number of applications. It is advantageous to inject vaccines into the skin as antigen which is then released into other tissues over a period of time, promoting the response by antibodies and T-cells. Assay sensors may also be injected into the skin, where they can be interrogated optically through the skin. Such assays are described for example in WO 00/02048 and PCT/EP01/11882. They may in particular be useful for glucose monitoring in diabetes. Cutaneous injection is also used cosmetically in wrinkle filling.

The depth at which material is injected is important, as it determines the layer of the skin in which the material will be deposited. The skin consists of two principal layers: the epidermis (upper layer) and the dermis (lower layer), with an overall thickness of 1.5 to 2 mm. The epidermis is overlaid by the stratum corneum, a layer of dead cells approximately 10 to 25 $\mu$m thick. The upper cells of the stratum corneum are continuously worn away. The epidermis and dermis are separated by the basement membrane at a depth of approximately 150 $\mu$m. The cells at the top of the epidermis progressively die and form the base of the stratum corneum, whilst the basement membrane generates new cells at the base of the epidermis. The dermis is vasculised, whereas the epidermis is not.

The fluorophores commonly used in the competition assays referred to above are illuminated transdermally with blue or green light, which has a low penetration depth. Melatonin, which absorbs UV and visible radiation, is produced by the basement membrane and transferred upwards into the epidermis to protect the skin from UV radiation. This melatonin absorbs blue and green illumination used to interrogate the sensors and the resulting fluorescence, and accordingly penetration through the skin is poor. Absorption of light by blood contributes to this effect. Therefore, the deeper the sensors are positioned in the skin, the weaker the fluorescence detection will be. Accordingly, for optimum sensitivity of the assay, the sensors should be as close to the skin surface as possible.

However, there are disadvantages associated with positioning the reagent particles within the epidermis or basement membrane. In particular, the concentrations of glucose within these layers may not correlate with the blood glucose concentration which the assay is attempting to measure. This is because the epidermis is not vasculised, and the basement membrane uses glucose in the production of epidermal cells which affects its glucose concentration. By contrast, the concentration of glucose in the interstitial fluid of the dermis is expected to correlate with blood glucose concentration. Further, if the reagent particles were positioned in the epidermis, they would move towards the skin surface as the epidermal cells were renewed. Glucose concentration in the epidermis is known to decrease towards the skin surface (and is zero at the stratum corneum), and this would cause complications. Particles injected into the dermis, on the ocher hand, will be retained permanently, as seen in a conventional tattoo.

In the light of these considerations, the optimum location for assay reagent particles is directly underneath the basement membrane, at the top of the dermis.

In other assays, it may be desirable for sensor particles to be deposited in the epidermis so that they will be expelled from the body over time (PCT/EP01/11822). Shallow injection may be achieved using an array of short needles coated with material to be injected. However, when injection is carried out with an array of this type material is deposited at every depth from the skin surface to the maximum penetration depth of the needle.

An apparatus or method, which provides injection to a pre-determined depth, is consequently desirable.

Accordingly, in a first aspect, the present invention provides an injection apparatus for making an injection at a predetermined depth in skin comprising:

a skin positioning member for positioning on a patch of skin within an area of skin to hold the patch of skin in a defined position, said skin positioning member being arranged such that at least a portion of said skin positioning member lies or is moveable to lie above or below said area of skin such that at least a part of said patch of skin is held elevated above or depressed below said area of skin, an injection needle, and means guiding said injection needle for movement from a parking position above the skin beside said skin positioning member to slide beneath said skin positioning member to an injection position in which the distal end of the needle lies at a predetermined distance below said skin positioning member.

Preferably, the apparatus further comprises means for attaching said skin positioning member to the skin.

Preferably, the needle is guided for movement of the distal end of the needle at a constant distance below the surface of the lifted patch of skin attacked to the skin positioning member. This will ensure that the injection depth is not dependent on the precise distance over which the needle point is moved, as would be the case if the needle moved obliquely with respect to the skin positioning member. Preferably, the skin positioning member holds the surface of the lifted area of skin flat. The movement of the needle is then preferably parallel to the skin position in a member surface.

The skin positioning member preferably has adhesive thereon to secure the patch of skin to the skin positioning member. Alternatively, the skin positioning member may be porous or provided with bores through which vacuum may be applied to hold the skin to the skin positioning member. In an alternative embodiment, the skin positioning member may be pressed against the patch of skin to depress the patch of skin.

The skin positioning member may be plate-like, or may form the surface of a non-plate-like member, for example a cone, a pyramid, a triangular prism or a hemisphere.

Preferably, said skin positioning member is moveable between a first position in which it lies on said area of skin and a second position in which at least a portion of said skin positioning member is elevated above or depressed below said area of skin with said patch of skin. However, the skin positioning member may be fixed in a position elevated above the surface of the skin and the skin may be drawn up to the skin positioning member by the application of vacuum and retained there against the skin positioning member by vacuum or by adhesive as described, or the skin positioning member may be fixed in a position depressed below said area of skin.

Preferably, means is provided for tilting said skin positioning member to elevate on edge thereof with said patch of skin attached thereto to lift said patch of skin. Alternatively, however, the whole skin positioning member may be elevated, with or without some tilting also, to raise the patch of skin. To conveniently provide for the tilting movement, said skin positioning member is preferably carried by a support structure to which the skin positioning member is hinged at one edge of the skin positioning member.

The skin positioning member may be moved using by the interaction of one or more cam followers carried by the skin positioning member each engaging a cam groove in a cam place which is mounted for sliding movement with respect to the skin positioning member.

The injection needle preferably is guided for movement using one or more cam followers attached to the needle each engaging in a cam groove in a cam plate mounted for sliding movement with respect to the needle and the same cam plate may control the movement of the skin positioning member and of the injection needle.

The apparatus may comprise a lower portion which is left on the skin after injection to define the injection site and an upper portion containing the injection needle which is detachable after injection. Said upper portion may further include said skin positioning member although this could be mounted to the lower portion so that it is left behind when the upper portion is removed. It could then either remain as part of the lower portion or be removed separately. If it were made transparent, it could remain covering the injection site and optical interrogation of an injected sensor could be made therethrough.

The predetermined depth at which injection is made using the apparatus is suitably in the range of 100 $\mu$m to 2 mm and may be fixed during manufacture or may be user adjustable.

Said injection needle is preferably carried by a syringe comprising a chamber for injectable material and means for dispensing said material through said needle. The syringe may contain as said injectable material particles to be injected and may contain in separate compartments said particles to be injected and a liquid for suspending the particles.

As indicated above, desirably the particles are assay sensor particles containing assay reagents. However, the injectable material in the syringe may alternatively he a medicament and may be an antigen for use in an immunisation.

The invention includes in an alternative aspect injection apparatus comprising a housing containing an injection needle mounted for guided movement from a parked position to an operative position, a detachable marker unit mounted to said housing and so positioned that said needle passes therethrough to reach said operative position, and means for securing said marker unit at an injection site prior to the making of an injection, whereby said apparatus can in use be positioned at an injection site, said marker unit can be secured at said injection site, said needle can be moved to said operative position to make an injection and said housing can be removed leaving said marker unit at the injection site to mark the position thereof.

Said marker unit may comprise a plate having an aperture therein through which the needle passes in use. Said aperture preferably has a maximum dimension of 2 m or less. Apparatus according to this second aspect of the invention may have all or any of the features described above in connection with the first aspect of the invention.

The invention further includes a method of fixed-depth cutaneous injection comprising: elevating or depressing a patch of skin without breaking the skin; holding the surface of the patch of skin in a defined position against the surface of a skin positioning member and guiding an injection needle beneath the skin positioning member to bring a discharge opening of the injection needle to a predefined location beneath the skin positioning member. This method may be carried out using apparatus according to the first and/or second aspect of the invention.

In a fourth aspect, the invention relates to a double chamber syringe comprising;
  a first chamber for a first injection component;
  a second chamber for a second injection component;
  a conduit for linking the first chamber and the second chamber and having a conduit inlet and a conduit outlet,
  at least one of the conduit inlet and the conduit outlet being obstructed by an obstruction member;
  a hollow needle extending from the second chamber; and
  a plunger forming a wall of the first chamber and operatively linked to the obstruction member or to the conduit;

wherein
  operation of the plunger causes:
  in a first step, movement of the obstruction member relative to the conduit such that the conduit inlet and conduit outlet are no longer obstructed and there is a fluid pathway from the first chamber to the second chamber via the conduit; and
  in a second step, reduction of the volume of the first chamber such that the contents of the first chamber are forced via the conduit into the second chamber where they mix with the contents of the second chamber, and the mixed contents are expelled via the needle.

Preferably, the obstruction member is a resilient stopper surrounding the conduit inlet and/or conduit outlet.

Preferably, the movement of the obstruction member relative to the conduit is a sliding movement.

Preferably, operation of the plunger also causes, in the first step, relative movement of the first chamber and the second chamber.

Preferably, the volume of the second chamber remains constant operation of the plunger.

Optionally, the conduit and the needle may be formed from a single tube with an obstruction between the conduit outlet and a needle inlet.

Optionally, a needle inlet or a needle outlet may be obstructed by an obstruction member.

In one preferred embodiment, operation of the plunger causes in the first step the first chamber to move from a first position wherein the conduit inlet is obstructed to a second position wherein the conduit inlet is no longer obstructed.

In a second preferred embodiment, operation of the plunger causes in the first step the conduit and the needle to move from a first position wherein the conduit outlet and a needle inlet are obstructed to a second position wherein the conduit outlet and a needle inlet are no longer obstructed.

Preferably, operation of the plunger also causes movement of the needle to an injection position, either before or during the first step. The needle may pass through an end cap. Preferably, operation of the plunger causes, in a third step, retraction of the second needle.

The syringe of the fourth aspect of the invention can be used in combination with the apparatus and method of any of the first, second and third aspects of the invention.

The invention will be further described with reference to the preferred embodiments shown in the accompanying drawings, in which.

Figure 1:
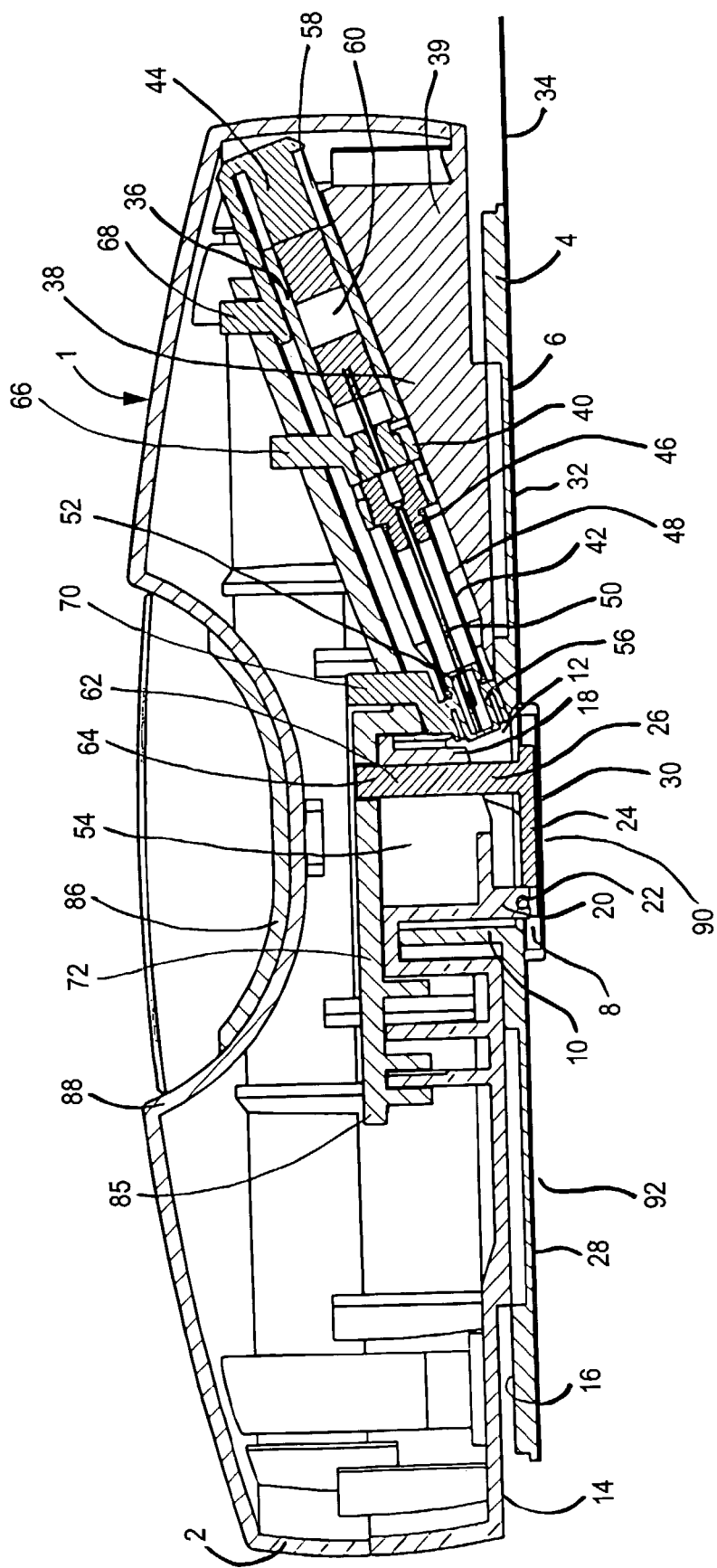
FIG. 1 shows a vertical cross section through an illustrative embodiment of the invention.
Figure 2:
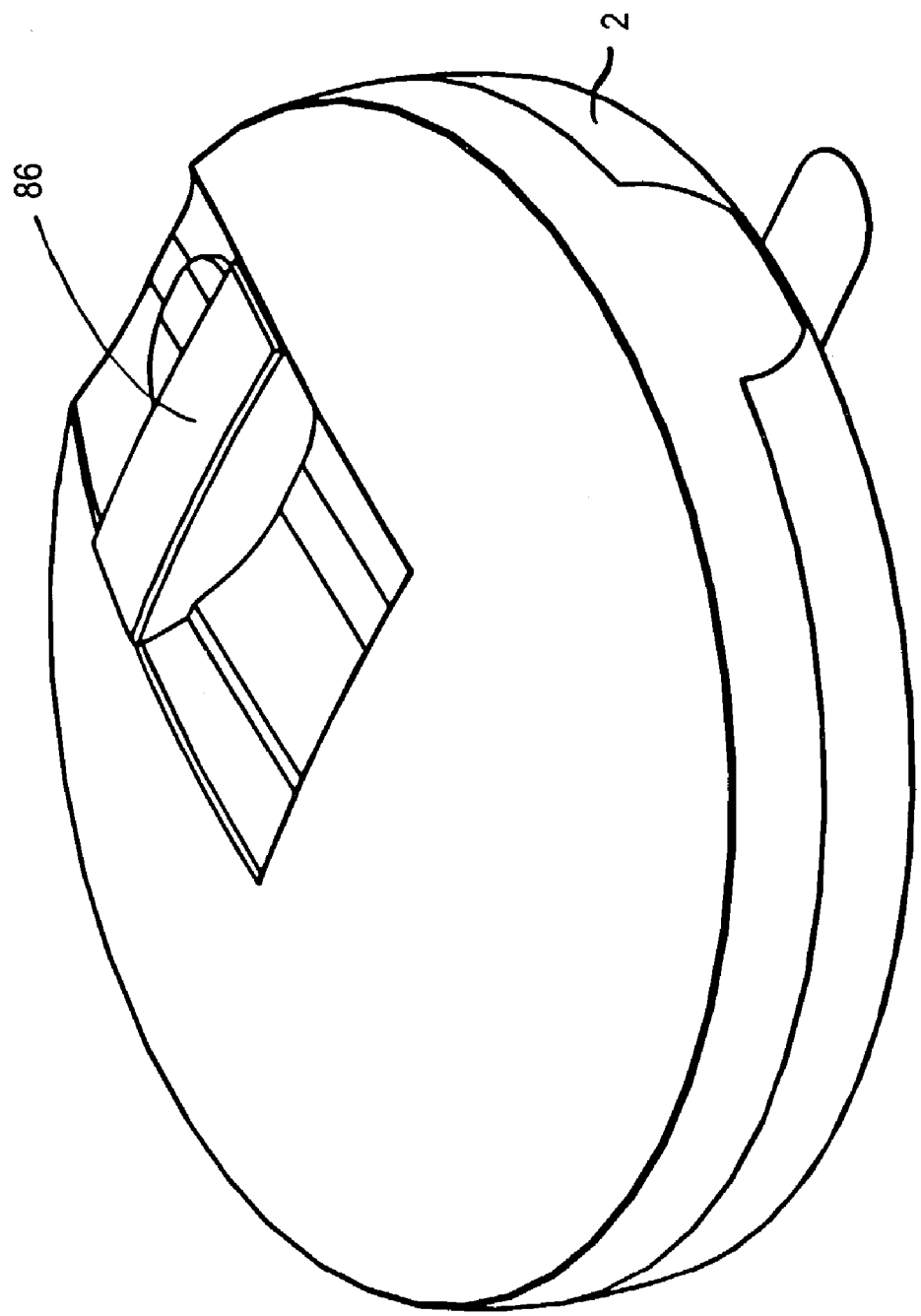
FIG. 2 shows the same embodiment in perspective view.

In a preferred embodiment of the present invention shown in the drawings, the injection apparatus 1 comprises an upper portion 2 and a lower portion 4. The lower portion comprises a circular place 6 having a central hole 8 defined by a cylindrical boss 10 with an aperture 12. The upper portion 2 is dome-shaped, and has a lower surface 14 which lies on the upper surface 16 of the lower portion 4. The upper portion 2 has a central cylindrical boss 19 extending downwards inside the boss 10 of the lower portion 4. The rim 20 of the upper portion boss 18 is attached by a pivot 22 to a skin positioning member constituted by a base plate 24 of a bell crank 26. The base plate 24 occupies the central hole 8 of the lower portion 4. The lower surface 28 of the lower portion 4 and the lower surface 30 of the base plate 24 have an adhesive covering 32, which is covered which a release cape 34.

The upper portion 2 comprises a syringe 36 mounted in a cylindrical sleeve 38 at an angle of approximately 20° to the lower surface 14 of the upper portion 2. The sleeve 38 forms an integral part of a wedge shaped block 39. The sleeve 38 has an axial slot 41 on its upper surface. The syringe 36 comprises a syringe body 40, a needle housing 42 and a plunger 44. The needle housing 42 extends from the lower end 46 of the syringe body 40, and comprises a collapsible sleeve 48 housing a needle 50 which is attached to the syringe body 40. At its distal end 52 the needle housing 42 passes through the aperture 12 and lies inside a chamber 54 defined by the lower portion boss 10, and is sealed with an end cap 56. The plunger 44 lies in the upper end 58 of the syringe body 40. The syringe body 40 contains material to be injected. In an alternative embodiment, the double chamber syringes described below may be used.

The upper portion 62 of the bell crank 26 forms a cam follower 64. Cam followers 66, 68, 70 are also mounted on the syringe body, the syringe plunger and the end cap respectively and protrude through the slot 41 in the sleeve 38. Each of the cam followers 64, 66, 68, 70 is constrained to radial movement in the direction 71.

A grooved cam plate 72 engages the cam followers 64, 66, 68, 70 to form a box cam. A cam groove 74 engaging cam follower 64 is initially angled to the left and then runs straight outwards towards the periphery of the apparatus 1. Cam grooves 76, 78 engaging cam followers 66, 68 initially run parallel to the final portion of the cam groove 74, then are angled to the left with the cam groove 78 engaging cam follower 68 more steeply angled, then parallel to the final portion of the cam groove 74. A cam groove 80 engaging cam follower 70 runs parallel to the final portion of the cam groove 74. The cam grooves 76, 78, 80 engaging cam followers 66, 68, 70 terminate in a common lateral cam groove 82 which is perpendicular to the final portions of the cam grooves 76, 78, 80. A spring (not shown) urges the cam followers 66, 68, 70 to the right. The cam plate 72 is mounted on runners 84 such that it is constrained to slide forwards and backwards in the direction 85 only. The cam plate 72 is attached on its upper surface 73 to a boss 87 which engages a manually engageable slider 86 on the upper surface 88 of the upper portion 2.

In use, the release cape 34 is removed from the adhesive covering 32 of the lower portion lower surface 28 and the bell crank base plate lower surface 30. The adhesive lower surface 28, 30 is applied to the skin. A small area of skin 90 becomes adhesively attached to the bell crank base place 24, and an annular area of skin 92 surrounding the small area of skin 90 becomes adhesively attached to the lower portion 4.

Figure 3:
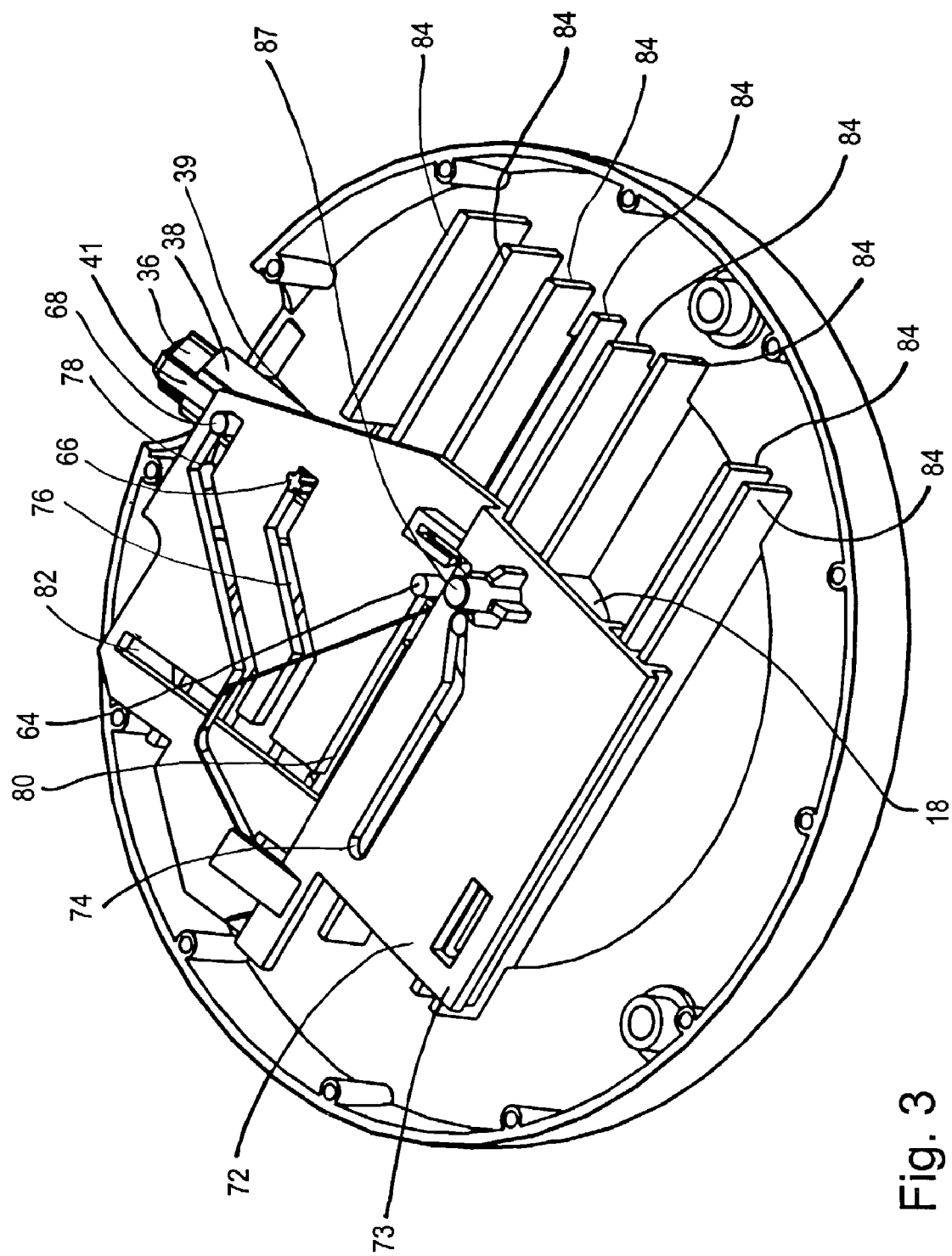
FIG. 3 shows the same perspective view but with some upper components removed.

To effect injection, the manually engageable slider 86 is pushed across the upper surface 88 of the upper portion 2 by the user. This causes the cam plate 72 to move forward along the runners 84 from its initial position shown in FIG. 3 to a final position. As the cam plate 72 moves, the cam follower 64 of the bell crank 26 is immediately moved to the left by the cam groove 74. This causes the bell crank 26 to rotate around the pivot 22, such that the base plate 24 of the bell crank 26 and the adhesively attached small area of skin 90 tilt relative to the lower surface 28 of the lower portion 4 to an angle of approximately 20°.

As the plate 72 continues to move forward, the cam follower 66 on the syringe body 40 is moved to the left by its cam groove 76. This causes the syringe needle 50 to move through the end cap 56 and into the chamber 54 defined by the lower portion boss 10, collapsing the needle housing 42. The needle 50 extends parallel to the lower surface 30 of the bell crank base plate 24 at a defined distance from it, such that it extends under the small area of skin 90 parallel to the skin surface at a defined depth. The depth may for example be 100 $\mu$m, which lies in the dermis just below the function with the epidermis. In an alternative embodiment, the distance between the bell crank base plate 24 and the needle 50 (and hence the depth of injection) may not be preset in manufacture but may be set by the user within a certain range, for example using a dial coupled to a screw jack lifting the needle assembly.

Simultaneously, the cam follower 68 on the syringe plunger is moved to the left by its cam groove 78. The steeper angle of this cam groove 78 compared with the cam groove 76 for cam follower 66 means that the syringe plunger 44 moves to the left relative to the syringe body 40 and travels down the syringe body 40. This causes the material 60 to be injected to be expelled through the needle 50 into the skin.

When the plate 72 reaches its final position, the cam followers 66, 68, 70 are forced to the right in the lateral groove 80 by the spring (not shown), retracting the syringe 36 into its sleeve 38. The syringe 36 is now shorter in length because the needle housing 42 has collapsed, and therefore the syringe 36 does not protrude into the chamber 54 defined by the boss 10. The upper portion 2 of the injection apparatus 1 can thus be removed from the skin surface. It is necessary to remove the adhesive coating 32 from the lower surface 30 of the bell crank base place 24 to achieve this.

The lower portion 4 of the injection apparatus 1 is left adhesively attached to the annular area of skin 92. Its central hole e is used to define the site of injection. This may be important, for example in the injection of assays which need to be interrogated optically or otherwise at the site of injection.

The preferred embodiment of the injection apparatus allows injection to a fixed depth to be achieved accurately. The system has several advantages over prior art method of injection. First, as the needle extends under the skin surface the site of entry of the needle is not near the site of injection. This may be important in optical interrogation of assays. Secondly, the channel depth of the needle in the skin is much larger than the injection depth. This means that a seal is formed between the skin and the needle, go that the material to be injected does not travel along the outside of the needle to the outside of the skin. Thirdly, injected material is often spread out because of the pressure of injection and the possibility of migration through tissue. This is particularly significant in vertical injection into the skin, where material often reaches the fat tissue below the skin which has a low resistance to flow. Using the present injection apparatus, even if the injected material is spread out, it will be spread horizontally at the same depth. When the apparatus is used to inject assay sensors, this has the advantage that there is no stray signal from sensors at depths ocher than the required depth.

In an alternative embodiment, the tiltable base plate 24 may be replaced by an inclined surface which is pressed against the skin surface to provide a fixed-depth injection path parallel to the inclined surface. The inclined surface may be the surface of a cone, the apex of the cone being pressed against the skin surface, or may be the surface of a flat plate pressed at an angle against the skin.

Figure 4:
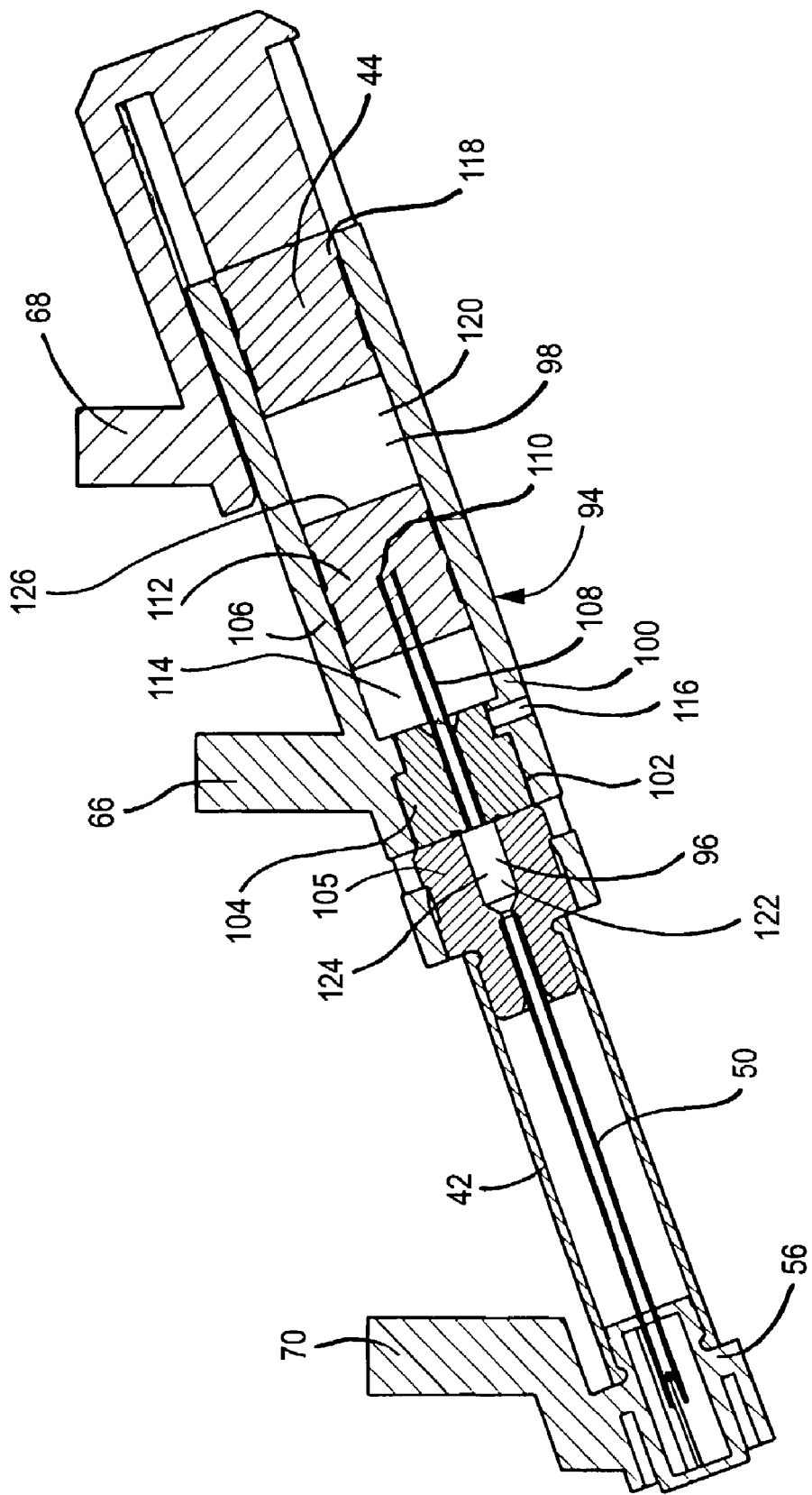
FIG. 4 is an enlarged view of the syringe component of the apparatus as shown in FIG. 1.
Figure 5:
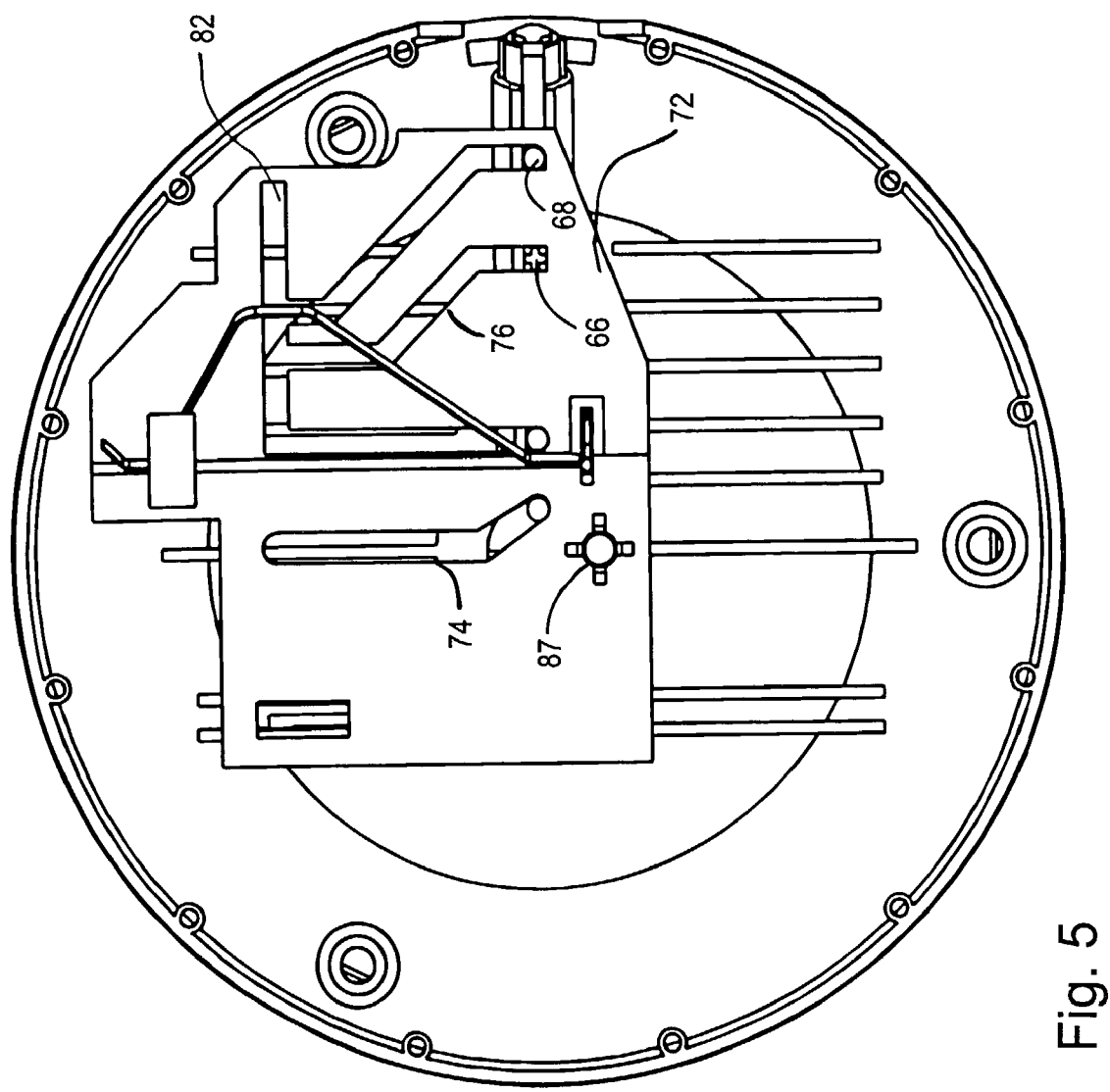
FIG. 5 is a plan view of the apparatus as shown in FIG. 3.

FIGS. 1 and 4 show a double chamber syringe 94 suitable for use with the preferred embodiment of the invention. This syringe 94 is used for injecting powder suspended in a liquid 98 which is kept separate from the powder 96 until the moment of injection. In alternative embodiments, the syringe may contain a liquid and two powders, two liquids and a powder, a solid dose and a liquid, a solid dose and a stiletto, or other materials to be injected.

The syringe 94 comprises a syringe body 40 having a shaft 100 closed at a first end 102 by a first needle supporting member 104 attached to a second needle supporting member 105. A cam follower 66 is mounted or the upper surface 106 of the shaft 100. The shaft 100 contains a first needle 108 protruding into the shaft 100 from the first needle supporting member 104 and embedded at its other end 110 in a needle cap 112 slideably mounted in the shaft 100. The first needle supporting member 104 and the needle cap 112 define an air space 114 in the shaft 100 which is connected to the outside by an air bore 116. A second end 118 of the syringe body shaft 100 contains a plunger 44, which is attached to a cam follower 68 on the upper surface 106 of the shaft 100. The needle cap 112 and the plunger 44 define a chamber 120 in the shaft 100 containing liquid 98.

A needle housing 42 an the form of a collapsible sleeve 38 extends from the second needle supporting member 105 away from the syringe body shaft 100. The distal end 52 of the needle housing 42 is closed by an end cap 56. A cam follower 70 is attached to the end cap 56. A second needle 50 extends from the second needle supporting member 105 into the needle housing 42. In the space 122 between the first needle supporting member 104 and the second needle supporting member 105, a chamber 124 between the first and second needles 108, 50 contains powder 96.

When the injection apparatus switch 86 is actuated as described above, the cam follower 68 on the plunger 44 and the cam follower 66 on the syringe body shaft 100 are simultaneously moved to the left. This causes the needle housing 42 to collapse such that the second needle supporting member 105 contacts the end cap 56 and the second needle 50 pierces the end cap 56 and extends outside the needle housing 42 into the site to be injected. Further movement left of the cam follower 68 on the plunger 44 causes the needle cap 112 (which is hydraulically locked to the plunger 44) to move along the shaft 100 into the air space 114 until it contacts the first needle supporting member 104. Air from the air space 114 is expelled from the shaft 100 through the air bore 116. As the needle cap 112 moves, the first needle 108 exits through the back surface 126 of the needle cap 112 into the liquid chamber 120. This creates a path from the liquid chamber 120 through the first needle 108, powder chamber 124 and second needle 50 into the site to be injected. Further movement left of the cam follower 68 on the plunger 44 causes the liquid 98 to move through the powder chamber 124, suspending the powder 96, and into the site to be injected.

Figure 6:
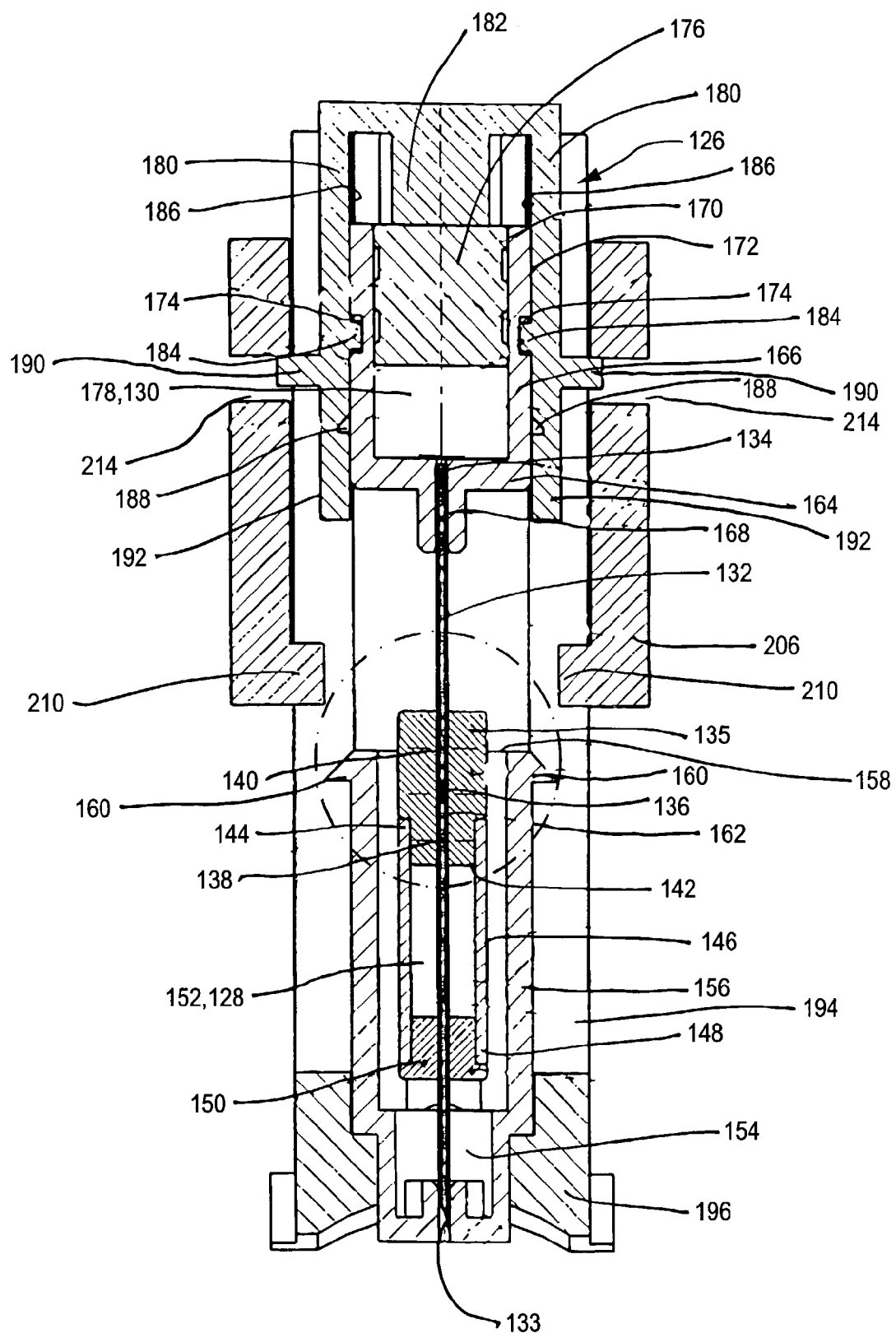
FIG. 6 is shows a cross-sectional view of an alternative syringe component to that of FIG. 4.
Figure 7:
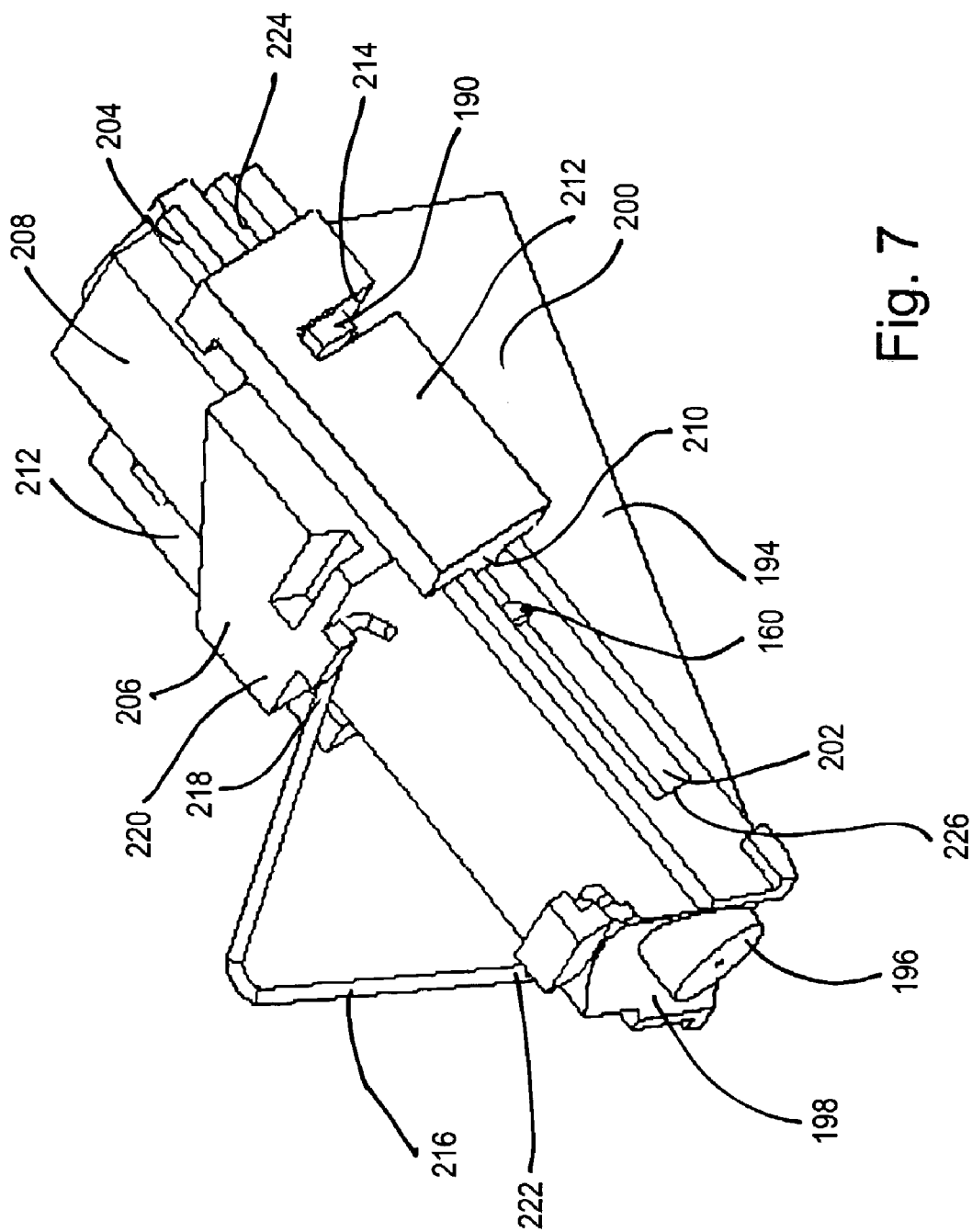
FIG. 7 shows a perspective view of the syringe of FIG. 6.

The alternative syringe component 126 shown in FIG. 6 is also used for injecting particles 128 suspended in a liquid 130 which is kept separate from the particles 128 until the moment of injection. As with the syringe component 94, the syringe may contain a liquid and two powders or types of particle, two liquids and a powder or particles a solid dose and a liquid, a solid dose and a stiletto, or other materials to be injected.

The syringe component 126 comprises a needle 132 having a front end 133 and a back end 134. The needle is centrally supported by a surrounding elastomer (e.g. rubber) stopper 135. The portion of the needle 132 lying within the stopper 135 contains an obstruction 136 occluding the bore of the needle 132. The obstruction 136 may for example consist of glue adhesive or a solid plug. The portion of the needle 132 also contains two through-going holes 138, 140, located to the front of the obstruction 136 and to the back of the obstruction 136 respectively. A front end 142 of the stopper 135 is sealed to a back end 144 of a tube 146 surrounding a portion of the needle 132. The tube 146 is sealed at its front end 148 by a second elastomer (e.g. rubber) stopper 150 surrounding the needle 132. The tube 146 and stoppers 135, 150 define a chamber 152 which is filled with particles 128. The front end 133 of the needle 132 is supported in a surrounding circular cylindrical needle guide 154. The needle guide 154, tube 146 and stopper 135 are surrounded by a cup-shaped housing 156 which is open at its back end 158. The back end 158 of the housing 156 is provided with two opposite wedge-shaped projections 160 on its outside surface 162.

The back end 134 of the needle 132 is mounted in a needle support 164 in the form of a circular cylindrical cup 166 having a stem 168 surrounding the needle 132 and open at the back end 170. The outside surface 172 of the needle support 164 is provided pith two opposite notches 174. A plunger 176 is slidably mounted in the needle support 164. The plunger 176 and needle support 164 define a second chamber 178 which is filled with liquid 130 and which is in fluid connection with the needle 132. The liquid 130 cannot escape from the front end 133 of the needle 132 as it cannot pass the obstruction 136 in the needle 132 and the through-going hole 140 in the needle 132 is sealed against the stopper 135.

Two opposite arms 180 extend from the back end 182 of the plunger 176 along the outside surface 172 of the needle support 164. Each arm 180 has an ear 184 on its inside face 186 which engages a notch 174 of the needle support 164 to lock the plunger 176 and needle support 164 together. Each arm 180 also has a wedge-shaped recess 188 on its inside face 186. Each arm 180 has a peg 190 protruding from its outside face 192.

The syringe 126 is mounted at an angle of approximately 20° to the lower surface 14 of the upper portion 2 of the device in a plastics wedge-shaped housing 194. An annular needle block 196 in which the needle guide 154 is mounted is mounted at a narrow end 198 of the wedge-shaped housing 194. Each side face 200 of the wedge-shaped housing 194 is provided with a slot 202 parallel to its sloping edge 204. The projections 160 of the housing 156 and pegs 190 of the arms 180 protrude into the slots 202. A sliding plate 206 is slideably mounted to the side faces 200 and top face 208 of the wedge-shaped housing 194 by means of sliders 210 engaged in each slot 202. The portions 212 of the sliding place 206 contacting the side faces 200 of the wedge-shaped housing 194 are each provided with a notch 214 which engages a peg 190. A cam follower (not shown) protrudes from the upper surface of the sliding plate 206 and engages the cam groove (not shown) of a cam place (not shown) operable using a manually engageable slider (not shown) as described in connection with the first preferred embodiment.

A bent wire spring 216 is attached at one end 218 to the portion 220 of the sliding plate 206 contacting the top face 208 and at the other end 222 to the narrow end 198 of the wedge-shaped housing 194. The spring 216 holds the sliding place 206 at the back end 224 of the slot 202.

In use, the sliding plate 206 is forced forwards along the wedge-shaped housing 194 by means of the manually engageable slider (not shown), compressing the spring 216. The pegs 190 of the arms 180 of the plunger 176 are engaged with the sliding plate 206, and thus the plunger 176 and locked needle support 164 are moved towards the front end 226 of the syringe 126. The needle 132 supported in the needle support 164 also moves towards the front end 226 of the syringe 126. The front end 133 of the needle 132 passes through the needle guide 154 and projects from the housing 194 to the injection site.

The stoppers 135, 150 and tube 146 move towards the front end 226 of the syringe 126 with the needle 132 until the stopper 150 contacts the needle guide 154. Further movement of the sliding plate 206 causes the needle 132 to slide through the stoppers 135, 150 such chat the through-going holes 138, 140 and obstruction 136 enter the chamber 152.

As the sliding plate 206 moves further, it causes the ends 228 of the arms 180 to contact the housing 156. The ends 228 are forced outwards by the wedge shaped projections 160 of the housing 156, distorting the arms 180. This distortion of the arms 180 frees the ears 184 from the notches 174 so that the plunger 176 is no longer locked to the needle support 164. As the sliding plate 206 continues to move forward, the arms 180 and plunger 176 move forward while the needle 132 and needle support 164 remain stationary. This decreases the volume of the chamber 178 such that liquid 130 is forced into the needle 132. The liquid 130 cannot pass the obstruction 136, and is therefore forced out of the needle 130 via through-going hole 140 into the chamber 152 of particles 128. The liquid 130 mixes with the particles 128. The mixed liquid 130 and particles 128 is forced by the pressure in the chamber 152 to enter the needle 132 via through-going hole 138 and is expelled via the front end 133 of the needle 132.

As the arms 180 move forward, the wedge-shaped recesses 188 of their inside faces 186 are forced over the wedge-shaped projections 160 of the housing 156. This locks the housing 156 to the arms 180.

As the sliding plate 206 reaches the front end 230 of the slot 202 the last liquid 130 and particles 128 are expelled from the needle 132. The force on the sliding plate 206 is released. The spring 216 acts on the sliding place 206 to force it towards the back end 224 of the slot 202. The engaged pegs 190 of the arms 180 move towards the back 232 of the syringe 126. The housing 156 is locked to the arms 180, and therefore also moves cowards the back 232 of the syringe 126 with the needle block 196. The housing 156 contacts the needle support 164 and forces the needle support 164 and the needle 132 towards the back 232 of the syringe 126. The needle 132 is thereby retracted into the wedge-shaped housing 194 after use.

Whilst the invention has been described which reference to the illustrated preferred embodiments, it is to be appreciated that many modifications and variations are possible within the scope of the invention.

What is claimed is:

1. Injection apparatus for making an injection at a predetermined depth in skin comprising:
   a skin positioning member for positioning on a patch of skin within an area of skin to hold the patch of skin in a defined position,
   said skin positioning member being arranged such that at least a portion of said skin positioning member lies or is moveable to lie above or below said area of skin such that at least a part of said patch of skin is held elevated above or depressed below said area of skin,
   an injection needle, and
   a guidance mechanism for guiding movement of the injection needle from a parking position above the skin beside said skin positioning member to slide beneath said skin positioning member to an injection position in which the distal end of the needle lies at a predetermined distance below said skin positioning member.

2. Apparatus as claimed in claim 1, further comprising an attachment element for attaching said skin positioning member to the skin.

3. Apparatus as claimed in claim 1, wherein the needle is guided for movement of the distal end of the needle at a constant distance below the surface of the lifted patch of skin attached to the skin positioning member.

4. Apparatus as claimed in claim 1, wherein the skin positioning member holds the surface of the lifted area of skin flat.

5. Apparatus as claimed in claim 1, wherein the skin positioning member has adhesive thereon to secure the patch of skin to the skin positioning member.

6. Apparatus as claimed in claim 1, wherein said skin positioning member is moveable between a first position in which it lies on said area of skin and a second position in which at least a portion of said skin positioning member is elevated above or depressed below said area of skin with said patch of skin.

7. Apparatus as claimed in claim 6, wherein a tilting mechanism is provided for tilting said skin positioning member to elevate on edge thereof with said patch of skin attached thereto to lift said patch of skin.

8. Apparatus as claimed in claim 6, wherein said skin positioning member is carried by a support structure to which the skin positioning member is hinged at one edge of the skin positioning member.

9. Apparatus as claimed in claim 6, wherein the skin positioning member is moved using by the interaction of one or more cam followers carried by the skin positioning member each engaging a cam groove in a cam plate which is mounted for sliding movement with respect to the skin positioning member.

10. Apparatus as claimed in claim 1, wherein the injection needle is guided for movement using one or more cam followers attached to the needle each engaging in a cam groove in a cam plate mounted for sliding movement with respect to the needle.

11. Apparatus as claimed in claim 10, wherein a single cam plate controls the movement of the skin positioning member and of the injection needle.

12. Apparatus as claimed in claim 1, comprising a lower portion which is left on the skin after injection to define the injection site and an upper portion containing the injection needle which is detachable after injection.

13. Apparatus as claimed in claim 12, wherein said upper portion further includes said skin positioning member.

14. Apparatus as claimed in claim 1, wherein the predetermined depth is in the range of 100 μm to 2 mm.

15. Apparatus as claimed in any claim 1, wherein said predetermined depth is user adjustable.

16. Apparatus as claimed in claim 1, wherein said injection needle is carried by a syringe comprising a chamber for injectable material and a dispensing mechanism for dispensing said material through said needle.

17. Apparatus as claimed in claim 16, wherein the syringe contains as said injectable material particles to be injected.

18. Apparatus as claimed in claim 17, wherein the syringe contains in separate compartments said particles to be injected and a liquid for suspending the particles.

19. Apparatus as claimed in claim 17, wherein the particles are assay sensor particles containing assay reagents.

20. Injection apparatus comprising a housing containing an injection needle mounted for guided movement from a parked position to an operative position, a detachable marker unit mounted to said housing and so positioned that said needle passes therethrough to reach said operative position, and a securing element for securing said marker unit at an injection site prior to the making of an injection, whereby said apparatus can in use be positioned at an injection site, said marker unit can be secured at said injection site, said needle can be moved to said operative position to make an injection and said housing can be removed leaving said marker unit at the injection site to mark the position thereof.

21. Apparatus as claimed in claim 20, wherein said marker unit comprises a plate having an aperture therein through which the needle passes in use.

22. Apparatus as claimed in claim 21, wherein said aperture has a maximum dimension of 2 mm or less.

23. A method of fixed-depth cutaneous injection comprising:

elevating or depressing a patch of skin without breaking the skin; holding the surface of the patch of skin in a defined position against the surface of a skin positioning member and guiding an injection needle beneath the skin positioning member to bring a discharge opening of the injection needle to a predefined location beneath the skin positioning member.

* * * * *